United States Patent
De Seixas Boavida Ferreira et al.

(10) Patent No.: US 9,241,446 B2
(45) Date of Patent: Jan. 26, 2016

(54) DIAGNOSTIC METHOD AND TREATMENT

(75) Inventors: Ricardo Manuel De Seixas Boavida Ferreira, Lisbon (PT); Sara Alexandra Valdas Da Silva Monteiro, Lisbon (PT); Maria Helena Mendes Da Costa Ferreira Correia De Oliveira, Vila Franca de Xira (PT)

(73) Assignee: INSTITUTO SUPERIOR DE AGRONOMIA, Lisbon (PT)

( * ) Notice: Subject to any disclaimer, the term of this patent is extended or adjusted under 35 U.S.C. 154(b) by 242 days.

(21) Appl. No.: 13/880,686

(22) PCT Filed: Oct. 20, 2011

(86) PCT No.: PCT/EP2011/068320
§ 371 (c)(1),
(2), (4) Date: Aug. 8, 2013

(87) PCT Pub. No.: WO2012/052506
PCT Pub. Date: Apr. 26, 2012

(65) Prior Publication Data
US 2014/0234438 A1    Aug. 21, 2014

(30) Foreign Application Priority Data

Oct. 21, 2010  (PT) .......................................... 105345
Oct. 27, 2010  (GB) .................................. 1018097.4

(51) Int. Cl.
*G01N 23/04*    (2006.01)
*A01G 7/06*     (2006.01)
(Continued)

(52) U.S. Cl.
CPC .. *A01G 7/06* (2013.01); *A01G 7/00* (2013.01); *G01N 23/046* (2013.01); *G01N 33/0098* (2013.01); *G01N 2223/419* (2013.01)

(58) Field of Classification Search
CPC ......... A01G 7/06; G01N 23/02; G01N 23/04; G01N 23/046; G01N 23/06; G01N 23/083; G01N 23/18; G01N 2203/0641; G01N 2223/419; G01N 2291/0238; G01N 2291/048; G01N 29/0672; G01N 33/0098; G01N 33/46
USPC ............................. 378/4, 21, 58, 62; 424/616
See application file for complete search history.

(56) References Cited

U.S. PATENT DOCUMENTS

| 4,078,087 A |   | 3/1978 | Hyman |         |
|-------------|---|--------|-------|---------|
| 4,144,673 A | * | 3/1979 | Quast et al. ..................... 47/57.5 |

(Continued)

FOREIGN PATENT DOCUMENTS

| EP | 1793225     | 6/2007 |
|----|-------------|--------|
| JP | 2006/078251 | 3/2006 |

(Continued)

OTHER PUBLICATIONS

Elhila et al., X-ray microtomography: application to a biological specimen, Sep. 1995, Bioimaging vol. 3, p. 103, 105.*

(Continued)

*Primary Examiner* — Irakli Kiknadze
*Assistant Examiner* — Julio M Duarte-Carvajalino
(74) *Attorney, Agent, or Firm* — Thorpe North & Western

(57) ABSTRACT

Methods for detecting early stage fungal infection (and especially esca or esca-like infections) in woody plants are disclosed, using X-ray tomographic imaging. In preferred embodiments, axial X-Ray tomography is employed, with radiodense regions of the tomograms indicating the location of such infection. The methods are particularly relevant to detection of esca in grapevine and kiwi. Methods for controlling such infections using such tomographic methods and direct introduction of fungicides are also disclosed.

22 Claims, 18 Drawing Sheets

(51) Int. Cl.
*A01G 7/00* (2006.01)
*G01N 33/00* (2006.01)

(56) References Cited

U.S. PATENT DOCUMENTS

| | | | |
|---|---|---|---|
| 4,283,629 A * | 8/1981 | Habermehl et al. | 378/4 |
| 8,106,252 B2 | 1/2012 | De Seixas Boavida Ferreira et al. | |
| 2010/0054543 A1 * | 3/2010 | Pachys | 382/110 |
| 2013/0051627 A1 | 2/2013 | Kim et al. | |

FOREIGN PATENT DOCUMENTS

| | | |
|---|---|---|
| WO | WO 91/05245 | 4/1991 |
| WO | WO 99/44050 | 9/1999 |
| WO | WO 2007/039537 | 4/2007 |

OTHER PUBLICATIONS

Di Marco et al., Pathogenicity of fungi associated with a decay of kiwifruit, Sep. 2004, Australasian Plant Pathology, vol. 33, p. 337, 338, 340, 341.*

Childs, J. F. L., Control of citrus blight disease, 1981, Proc. Fla. State Hort. Soc. vol. 94, p. 25-28.*

Mugnai et al., Esca (Black Measles) and Brown Wood-Streaking: Two Old and Elusive Diseases of Grapevines, May 1994, Plant Disease vol. 83 No. 5, p. 404, 405, 409.*

Bush, E. A., Botryosphaeria Canker and Dieback of Trees and Shrubs in the Landscape, 2009, College of Agriculture and Life Sciences, Virginia Polytechnic Institute and State University, bublication 450-726, p. 1, 2, 4.*

Aveskamp, et al., Biology and recent developments in the systematics of Phoma, a complex genus of major quarantine significance, Jul. 2008, Fungal Diversity, vol. 31, p. 1-18.*

Illman et al., Nondestructive Elemental Analysis of Wood Biodeterioration Using Electron Paramagnetic Resonance and Synchrotrons X-ray Fluorescence, Jun. 1997, International Biodeterioration & Biodegradation, vol. 39, No. 2-3, p. 239-241.*

Tomazello et al., Application of x-ray technique in nondestructive evaluation of eucalypt wood, 2008, Maderas Ciencia y tecnologia, vol. 10, No. 2, p. 140, 141, 147.*

Eranthodi et al., Thermotherapy for control of fungal pathogens in propagative Rootstocks of Horseradish, Apr. 2010, Hortscience, vol. 45, No. 4, p. 599, 600.*

Carter; The Status of *Eutypa lata* as a Pathogen; Phytopathological Paper No. 32; Jan. 21, 1991; 59 pages; International Mycological Institute/C.A.B. International, Oxon, UK.

Bieker, et al.; "Non-destructive monitoring of early stages of white rot by Trametes versicolor in Fraxinus excelsior"; 2010, Ann. For Sci, vol. 67, No. 210; pp. 1-7.

Brodersen, et al.; "The Dynamics of Embolism Repair in Xylem in Vivo Visualisations Using High-Resolution Computed Tomography"; Plant Physiology, vol. 154; No. 3; Nov. 2010; pp. 1088-1095.

Fromm et al.; "Xylem water content and wood density in spruce and oak trees detected by high-resolution computed tomography"; Oct. 2001; Plant physiology, vol. 127, pp. 416-425.

Larignon, et al.; "Esca et Black Dead Arm: deux acteurs majeurs des maladies du bois chez la vigne"; 2009; Conptes Rendus Biologies 332; pp. 765-783.

Luque et al.; "Symptoms and fungi associated with declining mature grapevine plants in northeast Spain"; 2009; Journal of Plant Pathology 91, vol. 2, pp. 381-390.

Mazliham, et al.; "Mass Function initialization rules for Ganoderma infection detection by tomography sensor"; 2006, Proc. Computational Intelligence, pp. 377-386.

McGovern et al; "Detection and assessment of wood decay using X-ray computer tomography"; 2010, Proc. of SPIE, vol. 7647; No. 1; 76474B-1-7647B.12.

Park, et al; "Hyaluronic acid of *Streptococcus* sp. As a potent elecitor for induction of systemic resistance against plant diseases"; World J. Microbiol. Biotechnol (2008) vol. 24, pp. 1153-1158.

Van Den Bulcke, et al.; "Three-Dimensional X-ray imaging and analysis of fungi on and in wood"; 2009 B, Microsocpy and Mycroanalysis; vol. 15, No. 5; pp. 395-402.

Yamada; "Defense Mechanisms in the Sapwood of Living Trees against Microbial Infection"; Journal of Forest Research, vol. 6, No. 3, pp. 127-137; 2001.

* cited by examiner (a)

(b)

(a)

(b)

(c)

(d)

(e)

(a)

(b)

(c)

(d)

(e)

(f)

(g)

(h)

(i)

(j)

(k)

(l)

DIAGNOSTIC METHOD AND TREATMENT

FIELD OF THE INVENTION

The invention relates to the diagnosis and treatment of fungal infections of woody plants, especially plants of the genus *Vitis, Actinidia* and *Citrus* and hybrids thereof, and especially fungal infections comprising Esca, Black Dead Arm (Botryosphaeriaceae fungi), or Esca-like infections, or infections with *Eutypa lata*.

BACKGROUND AND PRIOR ART KNOWN TO THE APPLICANT

Wood diseases caused by fungi are presently the most serious threat to the lifespan of commercial fruit trees and vines throughout the globe. They endanger the profitability and sustained production by decreasing yield and fruit quality, mainly by inducing the decay and death of infected plants. Key species affected by such diseases include grapevine (*Vitis* spp. and their hybrids), kiwi-fruit (*Actinidia* spp. and their hybrids), although it is increasingly recognised that similar diseases affect many other hosts, as will be discussed below.

In grapevine (*Vitis* spp. and hybrids thereof), esca, Petri disease, *Eutypa* dieback, and black dead arm (BDA) are the main wood diseases inducing such decay and death of the vine plants (Luque et al., 2009, "Symptoms and fungi associated with declining mature grapevine plants in northeast Spain", *Journal of Plant Pathology* 91, 381-390). As no effective control measures are available against these diseases, they are dramatically affecting the durability of the wine-growing heritage (Larignon et al., 2009, "Esca et Black Dead Arm: deux acteurs majeurs des maladies du bois chez la vigne", *Comptes Rendus Biologies* 332, 765-783.).

Esca is a complex grapevine wood disease that is achieving an unprecedented and increasing worldwide importance. First believed as affecting only mature grapevine, the disease is now found at high levels in much younger plants. It is accepted that esca comprises a number of distinct diseases and that the main causal agents (mostly vascular fungi) invade the vines not only through wounds in the field but also as a result of nursery practices. When infection starts in the nursery, plants may develop different diseases, ranging from Petri decline (also known as "black goo") to full-blown esca, with or without white decay of the woody tissues.

Esca is caused by the presence of at least three fungi, *Phaeomoniella chlamydospora, Phaeoacremonium aleophilum* and *Fomitiporia mediterranea*, acting alone, in combination or in succession. The two first fungi are responsible for vascular necroses, which appear as dark wood streaking, sometimes with some areas of dark and hard necroses, while *F. mediterranea* (and/or other wood-rotting basidiomycetes) induces white rot, or "amadou".

However, the pattern of symptoms and the initial onset of their expression are highly variable: severely infected plants can remain asymptomatic in successive years for a number of years without visible (leaf) symptoms of esca ("hidden" esca). This intermittent pattern of symptom expression leads infected plants to be indistinguishable from healthy ones.

It is of paramount importance to ensure healthy propagation of grapevine in the nursery, where only material without wood streaking should be selected. Once planted in the vineyard, infected propagating material develops Petri disease or decline, also characterised by wood dark streaking, slow dieback and "black goo". Because these fungi grow inside the wood of trunk and large wooden branches, one cannot reach them by foliage spraying with fungicides. The best remedy still is digging up the infected vine and burning it.

The greatest problem of esca derives from its initial stages: the plants are usually externally asymptomatic, although occasionally fruiting bodies and spores could be present. However, they are capable of disseminating the disease through common vineyard practice, such as pruning. In other words, a typical vineyard machine may pass on the disease from one infected, but asymptomatic, vine to the next ones. Spores are also disseminated by the wind and rain. Thus, while pruning tools and vineyard specialized machinery are not important in spore dissemination, they may play a role in spreading fungal mycelia from diseased plants to healthy ones. However, in what spore dissemination and penetration is concerned, pruning wounds and other wounds caused by vineyard specialized machinery are particularly important. For all these reasons, it is of paramount importance to develop methodologies capable of nondestructive screening and detection of the initial stages of esca, either in nurseries or in vineyards. Improved strategies and methods for treating such fungal infections at an early stage whilst eradication of the disease is still possible are also required.

Plant species other than grapevine are also subject to wood affecting, esca-like diseases. In 1999, a wood decay of kiwifruit vines (*Actinidia*) was noted for the first time in Italian vineyards. A similar disease was subsequently reported in Greece and New Zealand. Such diseases were described under the names of "esca-like" in France and "Elephantiasis" in Italy.

Analysis of kiwifruit vineyards exhibiting visual symptoms of esca-like disease revealed the presence of two types of necrosis in the wood: a) hard, brown decay initiating in the medular tissues and expanding gradually in the entire trunk or branches, and b) white and soft decay like "amadou wood" of grapevine. Isolations from necrotic parts of wood revealed a number of fungi, including *Fomitiporia mediterranea, Phaeoacremonium aleophilum, Phaeoacremonium parasiticum*, and *Cadophora malorum*. At least two of the above fungal species (*F. mediterranea* and *P. aleophilum*) are also involved in esca disease of grapevine, and aspects in common between the decay of kiwifruit and esca of grapevine can be hypothesized.

*Citrus* species (such as the orange cv. Washington navel, lemon and the common mandarin grafted on sour orange rootstocks) are experiencing a serious decline caused by *F. mediterranea*, in southern Greece orchards. Affected trees exhibit leaf chlorosis, defoliation, and death of shoots and twigs. Cross-sections of the trunks and large branches reveal a light-coloured rot in the centre, which is surrounded by brown hard necrotic wood. Symptoms start from pruning wounds and extend to the rootstock wood, resembling the esca wood symptoms of grapevine.

As well as grapevine, kiwi and *citrus*, esca-like diseases have also been identified in a number of other species. *Phaeoacremonium aleophilum* has been reported in *Prunus* species showing dieback symptoms in the Western Cape, South Africa. Serious dieback symptoms, caused by *Pm. parasiticum*, have been observed in cherry trees in Greece. *Phaeoacremonium mortoniae* was shown to cause brown wood staining of *Fraxinus pennsylvanica* and *Salix* spp.

One of the key causative agents, *Fomitiporia mediterranea*, is also found on *Corylus avellinus, Olea europaea, Lagerstroemia indica, Actinidia sinensis, Acer negundo, Olea europaea, Quercus* sp., *Quercus ilex, Ligustrum vulgare* and *Robinia pseudoacacia*.

A further plant disease, and similarly affecting woody species is Eutypiose, also known as "*Eutypa* dieback", is caused by the fungus *Eutypa lata*. *E. lata* is a vascular pathogen and occurs on at least 88 species of woody dicots (Carter, 1991. "The status of *Eutypa lata* as pathogen", *Phytopathological Paper* 32) and is responsible for significant economic damage mainly to grapevine and apricot.

Many forest and ornamental species also host the pathogen, but it is not certain whether all isolates are pathogenic, although pathogenicity of *E. lata* has been confirmed for grapevine, apricot, sweet cherry (*Prunus avium* L.), chokecherry (*Prunus virginiana* L. var. *demissa*), sour cherry (*Prunus cerasus* L.), almond (*Prunus dulcis*), apple (*Malus domestica* Borkh.), pear (*Pyrus communis* L.), walnut (*Juglans regia* L.), olive (*Olea europaea* L.), and *Ceanothus* L. spp.

On grapevine, the most recognized symptom of *Eutypa* dieback is the stunted appearance of shoots at the early growth season, with small, chlorotic and distorted leaves, and short internodes. However, the symptomatic expression fluctuates markedly from year to year. Non-destructive techniques for diagnosis of *Eutypa* dieback are still unavailable. Furthermore, no efficient treatment is available, and infected plants will die within a few years.

A further disease of concern, especially in grapevine (*Vitis*) is associated with infection by Botryosphaeriaceae fungi. These have a wide distribution and are commonly associated with dieback and cankers of woody and non-woody host plants, including forest trees, e.g. *Pinus* spp., *Eucalyptus* spp., *Quercus* spp., *Olea*, stone fruit trees, *Protea* and grapevine.

On grapevine, several species in Botryosphaeriaceae are associated with wood necrosis and they are also able to infect both young and mature tissues as well as green shoots causing cankers, vascular discoloration, and/or otherwise dark streaking of the wood.

Some Botryosphaericaeae species are responsible for Black Dead Arm (BDA) disease, in which the wood symptoms include V-shaped necroses, similar to those caused by *Eutypa lata*, and longitudinal brown streaking along the affected tissues. Other symptoms resembling *Eutypa* dieback, such as stunted chlorotic shoots, deformed leaves with necrotic areas are frequently observed.

It will be appreciated that all these diseases share common characteristics: (1) they are predominantly diseases of wood plants, and especially woody fruit-bearing plants of commercial importance; (2) they are fungal in origin, and (3) the pathogens invariably colonise the vasculature of the plant, especially the xylem. Furthermore, because (4) the disease symptoms are often localised—at least in the early stages—to the interior of the woody parts of the plant, non-invasive diagnosis of the conditions is difficult, if not impossible. In addition, once detected (5) treatment of the disease is difficult, because the internalisation of the fungal infection renders it barely susceptible to external application of fungicides.

In the wider context of diseases of the woody parts of commercially-important plants, one of the greatest problems facing agriculture is the fight against pathogens and insects that develop within the wood and so in a location where conventional fungicides/insecticides do not reach. It is therefore of great importance to develop methods to detect the existence, and the location, within infected plants, of wood diseases during the initial but asymptomatic and contagious phases of the infection (and thus, during a potentially treatable phase) and to develop treatment regimes that are effective against such diseases.

It is amongst the objects of the present invention to address these problems.

SUMMARY OF THE INVENTION

Accordingly, the inventors provide a method of detecting fungal infection in a woody plant comprising the use of X-ray tomographic imaging. A wide range of tomographic imaging methodologies are available, including X-Ray, PET (positron emission tomography), electrical resistance tomography and acoustic (including ultrasound) tomography. However, the inventors have found that the use of X-ray tomographic techniques including Computerised Axial Tomography (CAT), micro-computerised tomography, tangential scanning, simple radiography and multiple angle simple radiography allows externally asymptomatic plants to be diagnosed with a wide range of fungal infections.

In this way, the present method of the invention provides the possibility of detecting a fungal infection within such a plant, at a stage where it is possible to apply a treatment methodology at an early stage, i.e. where treatment is possible. If such diseases remain undetected, and therefore untreated, the plant will usually die, and will be a source of infection that may spread to other plants.

Whilst tomographic imaging has been used to image rot in wood caused by fungal decay of the dead woody material, and also the late stages of rot in dead areas of woody material in the trunks of growing trees, by contrast, the present invention relates to the early detection of fungal infection of live, growing plants susceptible to such infection by fungal plant pathogens. For example, U.S. Pat. No. 4,283,629 in the name of Habermehl describes a tomographic technique for detecting "red rot" in trees in which internal, dead woody areas within tree trunks can be detected by the decrease in radiodensity by comparison to surrounding healthy areas. The methods presented in this publication are directed towards commercial lumber production, to support commercial decision-making about when a wood-producing tree should be felled, and the extent to which its woody parts may be used in various manufacturing processes such as lumber or cellulose production.

In particularly preferred embodiments of the present invention said woody plant is a plant of the genus *Vitis* or a hybrid thereof, a plant of the genus *Actinidia* or a hybrid thereof or a plant of the genus *Citrus* or a hybrid thereof.

In any aspect of the invention, it is also preferred that said fungal infection is a fungal infection that causes accumulation or modification of fluid in the xylem of said plant. This fluid, such as the "black goo" seen in esca infection leads to a particular characteristic response in the tomographic image, allowing it to be differentiated from other internal features such as fungal rot.

Accordingly, it is particularly preferred that said fungal infection comprises Esca or an Esca-like disease.

In further preferred aspects of the invention said fungal infection comprises infection with *Eutypa lata*, or *Botryosphaeria*-associated canker (or generally infection with fungi of the Botryosphaeriaceae family), or infection with *Phoma tracheiphila*.

In any aspect of the invention it is particularly preferred that said tomographic imaging comprises axial X-ray tomography. Axial X-Ray tomography has been shown by the inventors to be particularly effective at identifying regions of plant material, especially those not visible on the exterior of the plant, that are colonised by plant pathogenic fungi.

In particularly preferred aspects of the invention, the inventors provide such a method using X-Ray tomography, and especially axial X-Ray tomography or X-Ray microtomography, wherein said method comprises the steps of: obtaining a tomographic image of a stem of said woody plant, said tomographic image comprising spatially-distributed measurements of radiodensity; determining the presence or absence of regions within said image having a radiodensity larger than a first predetermined radiodensity; the presence of such regions of high radiodensity being indicative of the presence of said fungal infection.

Unusually, the inventors have found that such X-ray tomographic images reveal regions of living plant material that are colonised by fungal pathogens and, especially in the case where the fungal pathogens colonise the vasculature of the plant with subsequent production of fluid within the vasculature or chemical modification of fluid within the xylem (e.g. by production of polyphenolic material or gums), this is revealed by regions of increased radiodensity. The fungal pathogens are prone to induce the production of radiodense material within the vasculature (i.e. more radiodense than the fluid usually found in e.g. the xylem of the plant) that leads to a positive indication of such an infection. By way of contrast, previous use of X-ray tomography to image decay in dead wood (e.g. in building materials or in living trees in urban areas) detects the area of rot as regions of very low radiodensity, in fact producing little or no signal by comparison to the signal produced in the absence of wood. It is often not possible, therefore, to differentiate the presence of decay in dead wood (e.g. by soft rot fungi) from holes within the wood itself.

In such a method, it is particularly preferred that said first predetermined radiodensity is the mean radiodensity of a corresponding region in an uninfected control plant. In this way, the method may be readily adapted for application in a range of woody species by calibrating the tomographic images against images taken of healthy plants.

Preferably, in any such method, and especially in the case of grapevine said first predetermined radiodensity comprises 100, 120, 130, 140, 150, 160, 170, 180, 190 or 200 Hounsfield units.

Hounsfield units are well known in the field of X-Ray tomography, and are a linear transformation of the radio attenuation coefficient within the material, scaled with respect to the corresponding attenuation in air and water, as follows:

$$R=1000*(\mu_x-\mu_w)/(\mu_w-\mu_a)$$

Where: R is the radiodensity in Hounsfield Units
$\mu_x$ is the linear attenuation coefficient in the sample
$\mu_w$ is the linear attenuation coefficient of water
$\mu_a$ is the linear attenuation coefficient of air In further preferred embodiments, the inventors provide such a method further comprising the step of: determining the presence or absence of regions within said image having a radiodensity less than a second predetermined radiodensity; the presence of both such regions of high and low radiodensity being indicative of the presence of an advanced stage of said fungal infection. Preferably, said second predetermined radiodensity comprises −200, −300, −400, −500, −600, −700, or −800 Hounsfield units.

In any aspect of the invention, it is preferred that said radiodense regions have a spatial dimension of less than 5 mm, 2 mm, 1 mm, 500 microns, 200 microns 100 microns or even 50 microns. The inventors have found that the radiodense regions correspond to accumulation of a "block goo", predominantly of plant origin, and likely to comprise an excretion of polyphenolic compounds secreted by the plant as part of a host defense mechanism. The fluid accumulates primarily in the xylem vessels of the plant, and so the radiodense regions reflect the narrow, elongate nature of the vasculature. At least one of the spatial dimensions (width, height, and length) of the radiodense regions is therefore of a small dimension as recited above. The inventors have found that these regions may be imaged by the techniques described herein, and are particularly indicative of esca and esca-related infections.

Such a method is particularly applicable to fungal infections like esca or esca-like infections where accumulation of radiodense material in the vasculature of the plant is followed, during development of the infection, by the appearance of regions of rot of dead tissue within the plant structure, such as those referred to as "Amadou" in esca in grapevine. In this way, the presence of both regions of relatively high and relatively low radiodensity can detect a particularly advanced stage of such a fungal infection. This can aid with decision-making regarding remedial action to be taken, such as treatment of the infected plant, or a decision to uproot and replace the plant.

Also in any aspect of the invention, it is preferred that said stem has a diameter of between 1 and 10 cm. The rationale for the disclosed testing methodology is to be able to treat infected woody plants, and especially vines, and the use of the technique on relatively small stems is of assistance in identifying the disease at an early stage.

Also in any aspect of the invention, it is preferred that said woody plant comprises rootstock or graft material, and said stem has a diameter of less than 1 cm. The inventors have found that the techniques disclosed herein allow the rapid screening of rootstock and graft material, typically having stem diameters below 1 cm, as they leave nurseries. This is especially true in the case of vines, where it is vital to prevent infected material leaving vineyard nurseries providing a possible source of infection to otherwise healthy plants.

The availability of such methods to diagnose these devastating diseases in commercially-important species leads the inventors to be able to provide hitherto unavailable strategies and methods for management of such diseases in woody species.

Accordingly, the inventors provide a method of control of fungal infection in woody plants comprising the steps of: determining the presence or absence of said fungal infection using a method according to any of the methods disclosed herein; and treating said woody plant with a fungicide, and preferably a systemic fungicide if said fungal infection is so detected.

In any aspect of the invention, a range of fungicides are envisaged, and may be selected by the skilled addressee on the basis of their efficacy against the particular fungal pathogen to be treated. Amongst the families of fungicides available to the skilled addressee are Copper based products; Anilinopyrimidines Azoles and non-azoles (ergosterol biosynthesis inhibitors); Carboxamides; Phenylpyrroles; Phosphonates; pyridinyl ethylbenzamides and QoI—Strobilurins.

Particular examples of such fungicides include Cyprodinil, fludioxonil, pyraclostrobin, boscalid and mixtures thereof (cyprodinil+fludioxonil and pyraclostrobin+boscalid), tebuconazole, phosphonates.

There are also further compounds having fungicidal activity, but not specifically registered as fungicides, such as: baking soda (sodium bicarbonate, $NaHCO_3$) and potassium bicarbonate ($KHCO_3$) and hydrogen dioxide (hydrogen peroxide).

Fungicides having plant growth promotion activity are particularly preferred, such as blad. Blad is a polypeptide extractable from cotyledons of *Lupinus albus*, or producible by use of recombinant DNA technologies. Details of Blad are given in co-pending International Patent Application WO2007010459.

Fungicides with a host defense-inducing activity, such as Chitosan, are also particularly preferred.

Also fungicides having a host defense-inducing activity, in addition to some direct effects on fungi, are particularly preferred, such as hyaluronic acid (an elicitor for induction of systemic resistance. See *World J Microbiol Biotechnol* (2008) 24:1153-1158) or acibenzolar-S-methyl.

Preferably, said fungicide is injected into said plant. By "injected", we mean that such a fungicide is introduced directly into the internal region of the plant where the tomographic imaging has detected the fungal infection. As well as literally injecting such a fungicide, other means may be employed, such as drilling a hole in the stem or trunk of the plant, and dispensing the fungicide therein. A plug of slow-release fungicide is envisaged as being particularly advantageous.

In particularly preferred embodiments of the invention, the tomographic image is used to identify the region of the plant in which the infection is located (by the regions of relatively high radiodensity), and fungicide is introduced directly into these regions.

BRIEF DESCRIPTION OF THE DRAWINGS

The invention will be described with reference to the accompanying drawings, in which.

DESCRIPTION OF PREFERRED EMBODIMENTS

Figure 1:
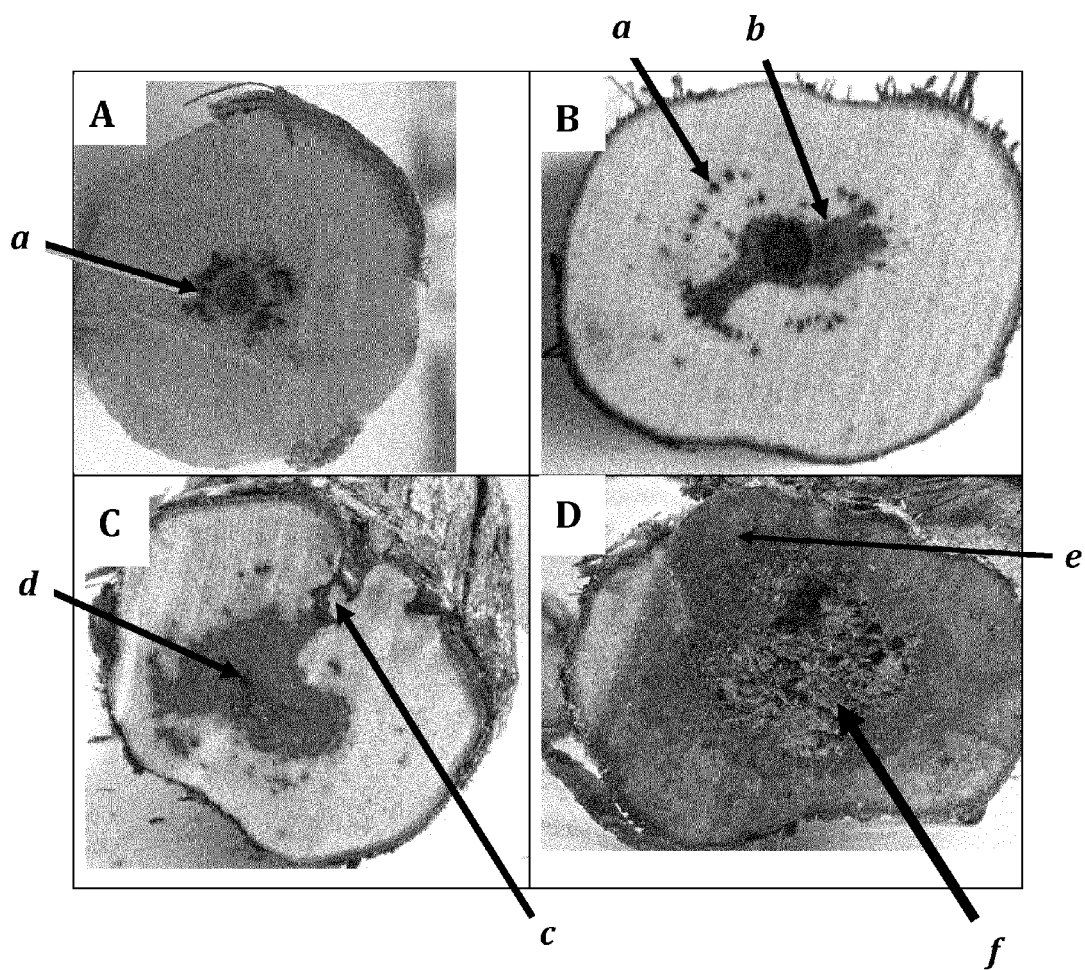
FIG. 1 shows photographs of cross-sections through esca-infected grapevine stems.

FIG. 1 illustrates, photographically, a typical progression (from A to D) of esca infection in grapevine wood along with some characteristic structural features of wood in its diseased state. FIG. 1A shows a section through a grapevine in its initial stages of infection, showing black spots (a) in an apparently healthy wood background. FIGS. 1B, and 1C show intermediate stages of esca infection, having black spots (a) and brown affected wood (b) as well as scars (c) and pith (d) that are normal features of wood. FIG. 1D shows final stages of esca infection with dead wood (e) and "Amadou" (f). It can be clearly seen that, in the earlier stages of infection (FIGS. 1A and 1B), the infection is localised within the interior of the woody parts of the vine. No external symptoms are present towards the periphery of the wood, and so no visible signs of infection are apparent on the plant.

Figure 2:
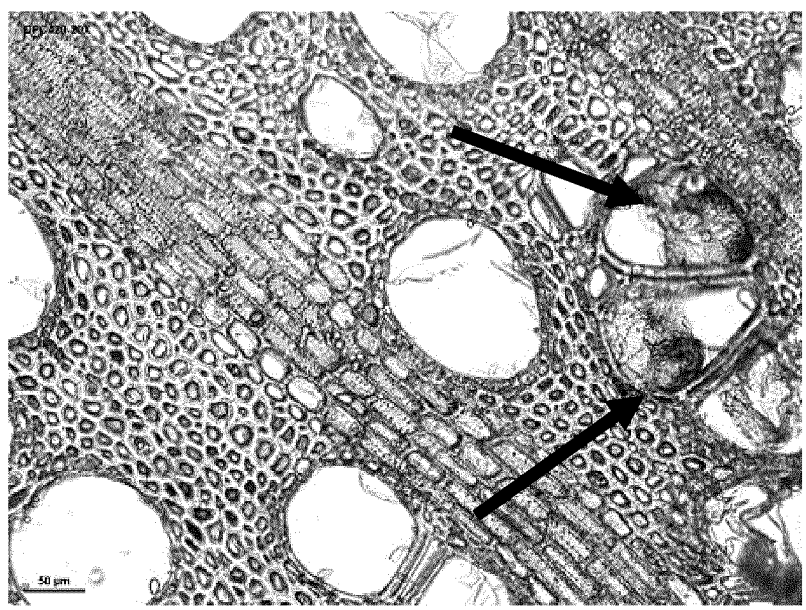
FIG. 2 is an optical micrograph of an esca-infected grapevine.

Optical microscopy of a section of an esca-infected, asymptomatic grapevine reveals (in FIG. 2) the presence of "black goo" within the lumen of tracheids and xylem vessels of the plant (black arrows). It is the presence of this comparatively radiodense material that may be detected using tomographic imaging, and especially X-Ray tomographic imaging.

Figure 3:
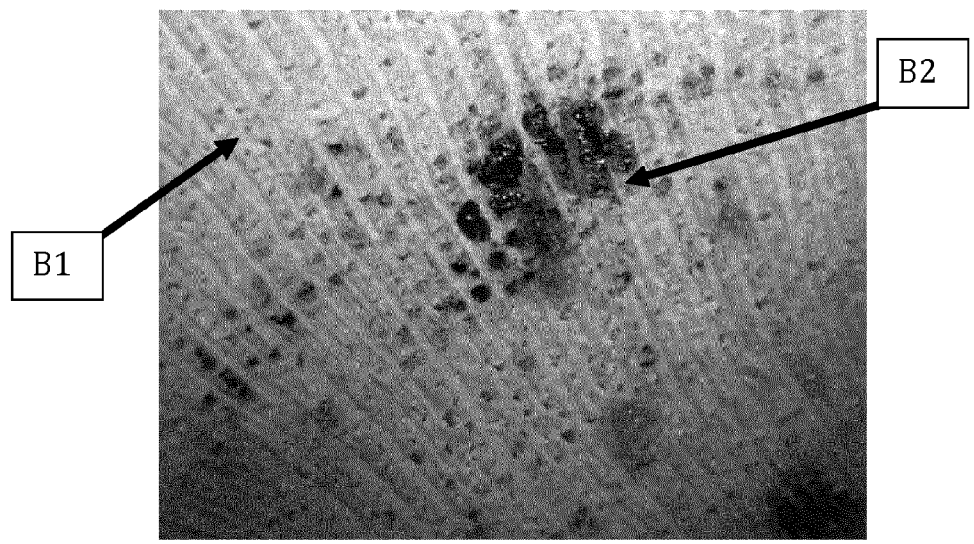
FIG. 3 shows photographs of "black goo" in the vasculature of esca-infected grapevine.
Figure 3:
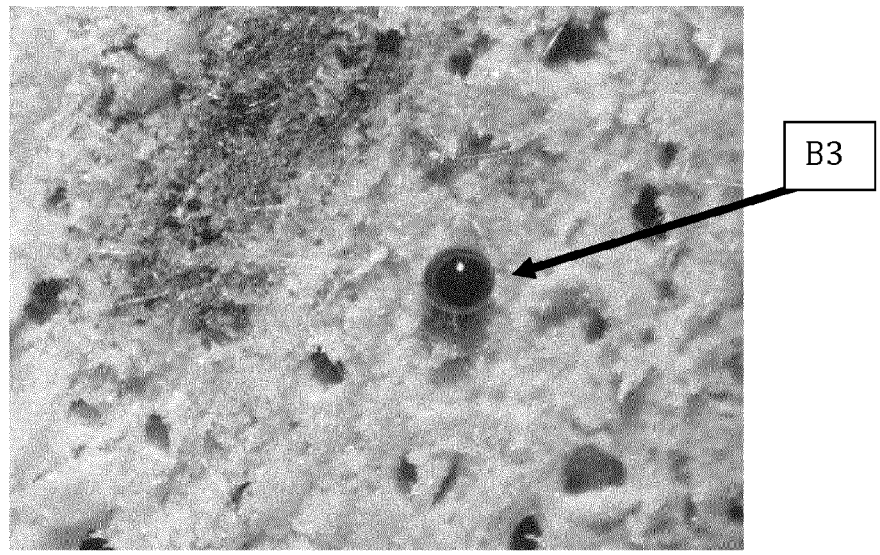

FIG. 3 shows the presence of "black goo" within, and exuding from, xylem vessels in a cut section of esca-infected grapevine wood. In FIG. 3($a$) a peripheral region of the stem (B1) shows healthy, uninfected grapevine wood, whereas the dark region (B2) shows "black goo" within the xylem. In FIG. 3($b$), the "black goo" is seen to be exuding (B3) from the xylem vessels.

Figure 4:
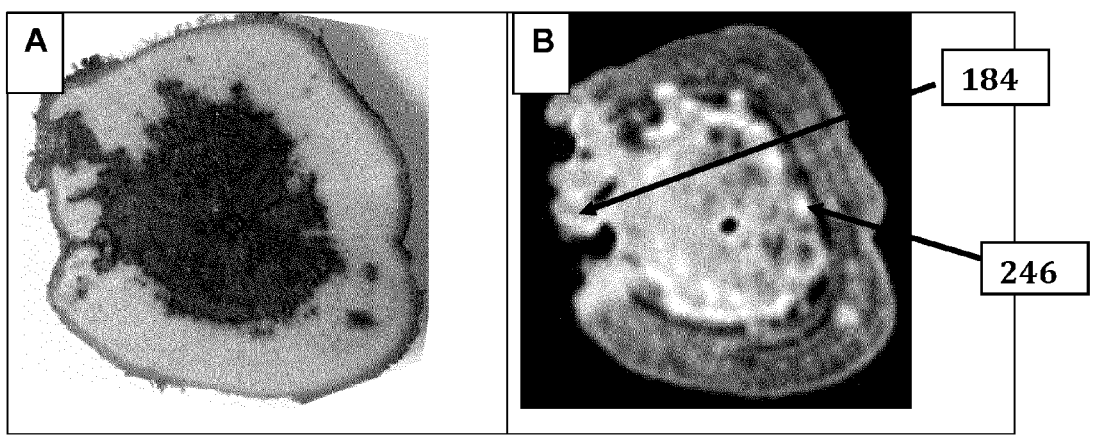
FIG. 4 shows a photograph and corresponding X-ray tomograph of an esca-infected grapevine.

FIG. 4A is a photograph of a cross-section of an esca-infected trunk of grapevine at an intermediate stage of infection, taken after previous CAT (Computerised Axial Tomography) analysis of an intact esca-infected grapevine trunk. FIG. 4B is a tomographic image obtained by axial X-Ray tomography according to the present invention. The tomographic image (4B) shows radiodensity according to the scale presented on the right hand side of FIG. 5D. Dark colours are indicative of regions of low radiodensity, with lighter areas indicating increasing levels of radiodense material. Black in the image represents a radiodensity of approximately −135 Hounsfield units, with white representing approximately +215 Hounsfield units. Images were obtained by use of a Phillips TOMOSCAN AV computer axial tomography apparatus. Images were obtained with the following parameters:

Scan: 120 kV, 90 mA, 2 s

Tilt: 0.0°

Depending on the size of trunk to be imaged, the following apertures were used:

250 mm/1.2

270 mm/1.1

160 mm/1.9

FIG. 4B graphically illustrates the ability of axial X-ray tomography to detect signs of esca infection within the core of woody material, by virtue of the radiodense material "black goo" within the vascular system of the plant. The radiodensity values of two points within the image are given (184 and 246 Hounsfield units), indicative of regions having vasculature filled with the "black goo" characteristic of esca infection.

Figure 5:
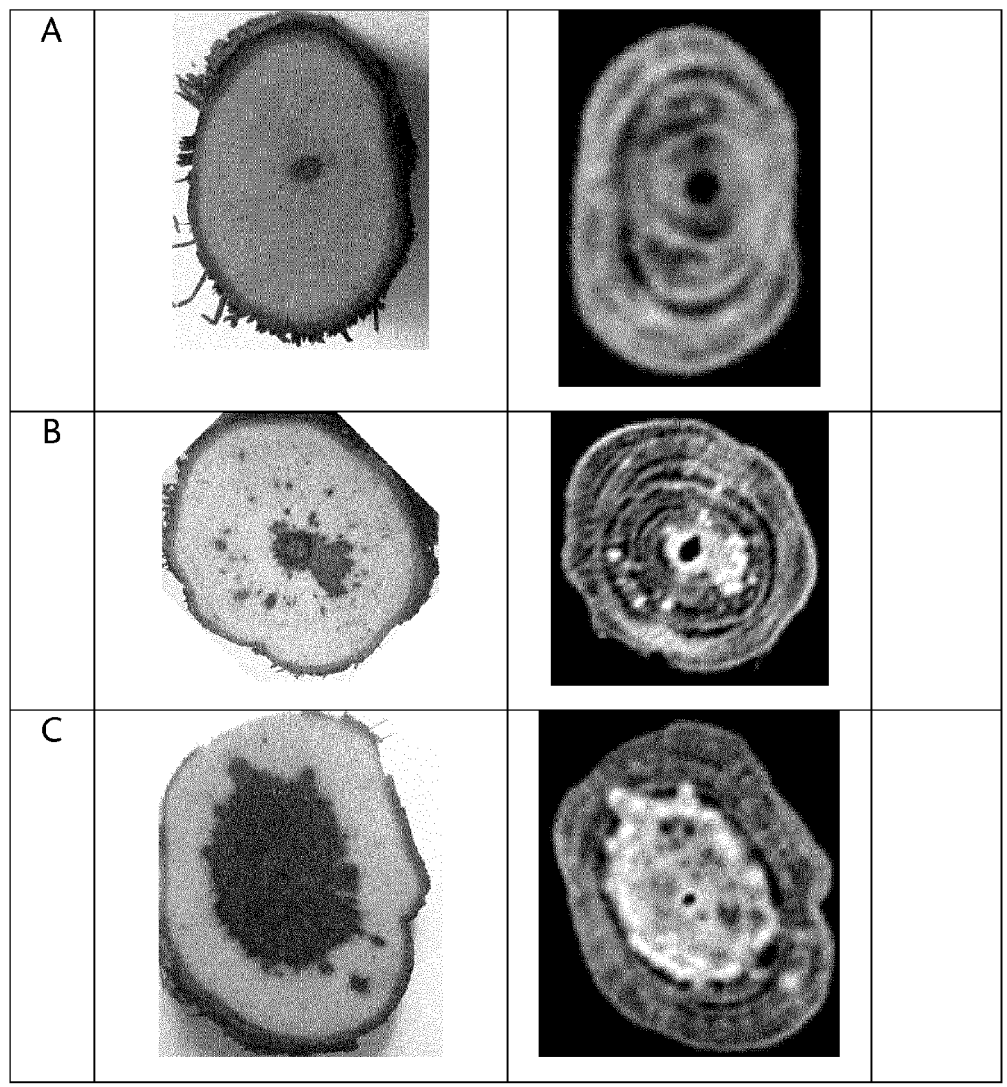
FIG. 5 shows photographs and corresponding X-ray tomographs of grapevine stems in various stages of esca infection.
Figure 5:
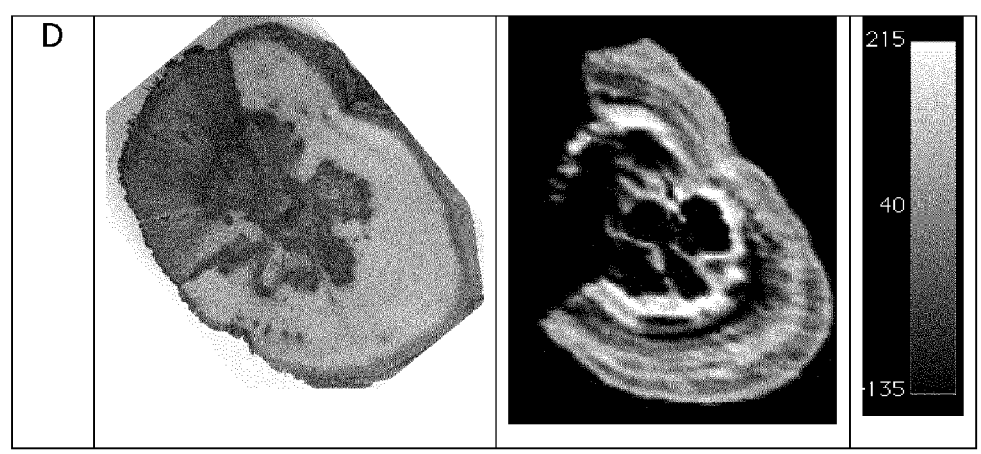

FIG. 5(A-D) illustrates photographs of cross-sections (left-hand column) of grapevine wood with various degrees of esca infection, together with computer axial X-Ray tomographic images (right-hand column) obtained before the wood was sectioned for photography. The tomographic images show radiodensity maps of the wood, according to the scale adjacent FIG. 5D, with dark regions representing low radiodensity and light regions a corresponding high radiodensity. Black regions have a radiodensity of −135 Hounsfield units or below, with white regions having a radiodensity of 215 Hounsfield units or above.

FIG. 5A shows images of a healthy, uninfected stem; FIG. 5B is of a stem during the initial, asymptomatic stages of infection. Particularly evident are the regions of high radiodensity (white areas in FIG. 5B radiodensity map) that correspond with the black areas in the corresponding photograph, and comprising regions of vascular tissue having "black goo" within the xylem, as well as the areas of brown affected wood surrounding them.

The images of FIG. 5C correspond to a stem at an intermediate stage of esca infection. Again, the areas of high radiodensity shown as light-coloured regions correspond to the radiodense dark regions comprising "black-goo" filled regions of the woody stem shown in the photograph.

Finally, the images of FIG. 5D correspond to a stem at an advanced stage of esca infection. As well as regions of high radiodensity (the light-coloured patches in the tomograph)

corresponding to filled vasculature, the images also show (on the left hand side) regions of low radiodensity (the dark, or black regions in the tomograph) that correspond to white rot affected areas or "amadou" shown in the photograph.

The images demonstrate the ability of computer axial X-Ray tomography to non-invasively identify early stages of esca infection through detection of regions of high radiodensity, as well as to identify later stages of infection through the detection of regions of low radiodensity, corresponding to "amadou".

FIG. 6(a)-(e) show patterns of radiodensity obtained by X-ray based computerised axial tomography of in intact, healthy grapevine stem. The graphical representation of the radiodensity corresponds to the section illustrated on the 2-D tomographic image illustrated by a light-coloured line. The spot on the 2-D image is represented by the vertical reference line on each graph, with the corresponding horizontal line giving the spot radiodensity measurement expressed in Hounsfield units.

In each graph, the range of radiodensities illustrated is plotted on a scale of −478 to +173 Hounsfield units, and the "spot values" are as follows:

| FIG. | Spot Value (Hounsfield Units) |
|---|---|
| 6(a) | +119 |
| 6(b) | −46 |
| 6(c) | −478 |
| 6(d) | +125 |
| 6(e) | +25 |

Figure 6:
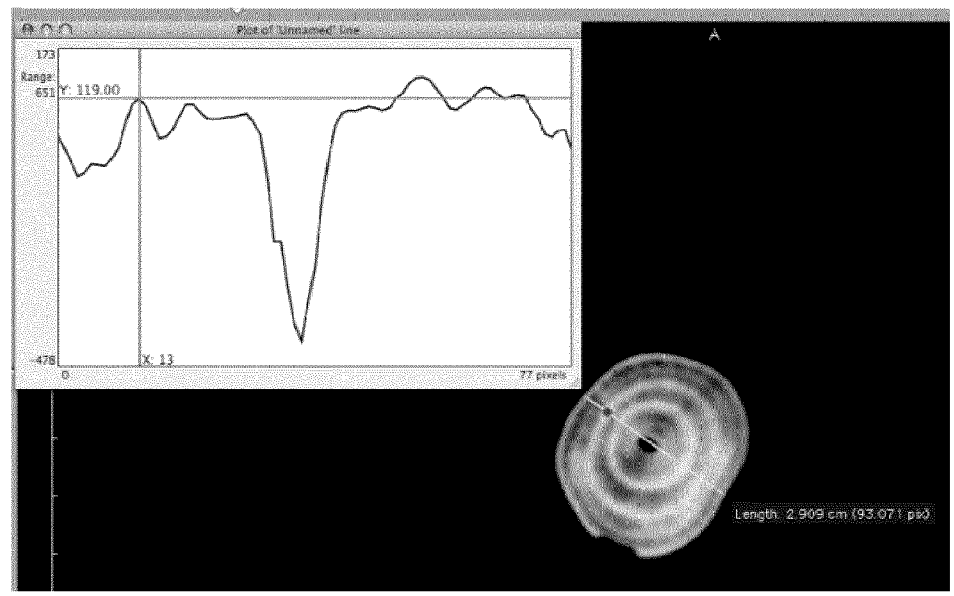
FIG. 6 is a series of tomographs and radiodensity graphs through healthy grapevine stems.
Figure 6:
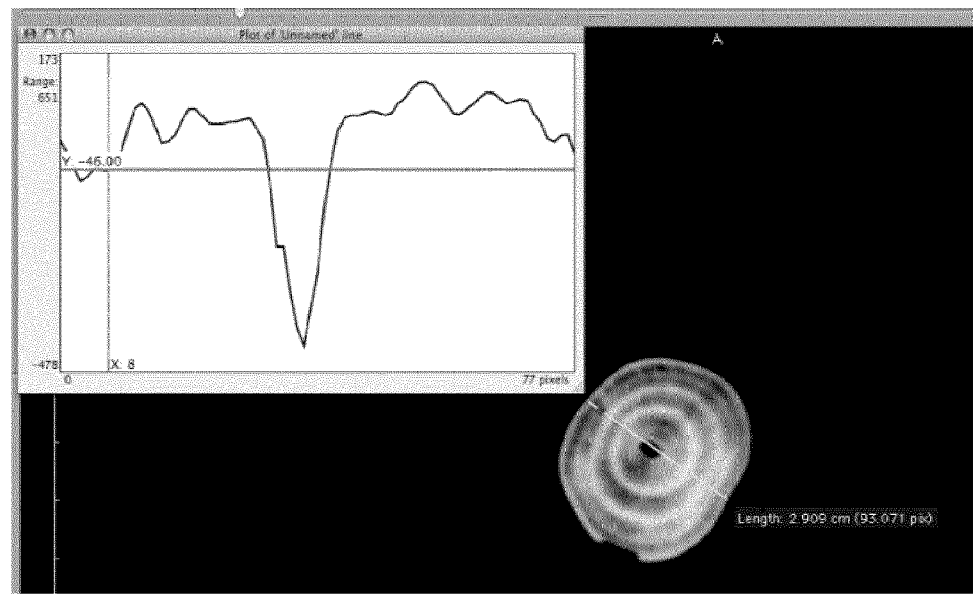
Figure 6:
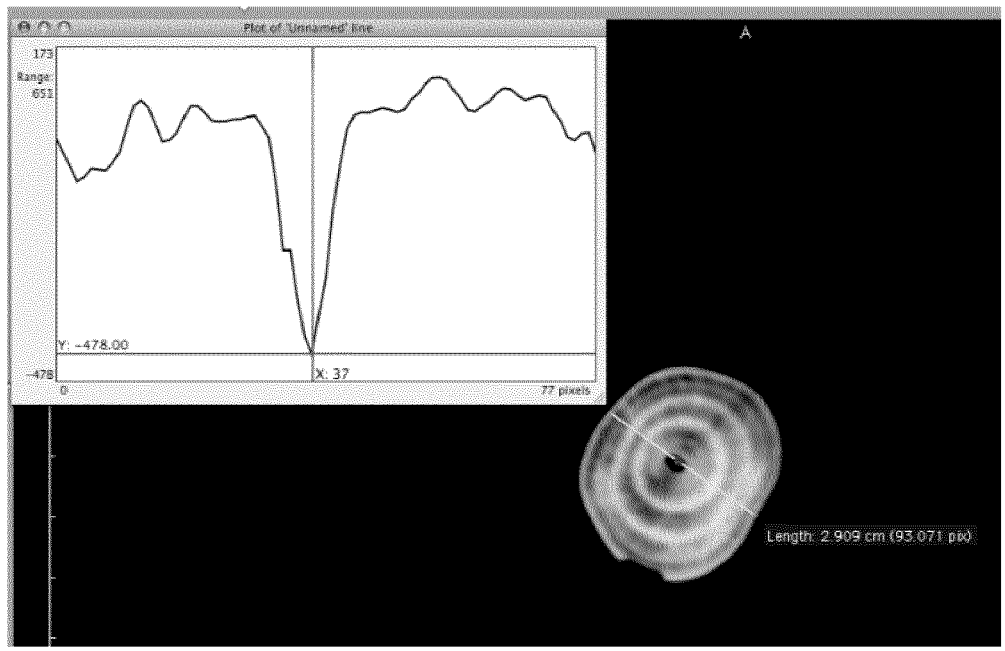
Figure 6:
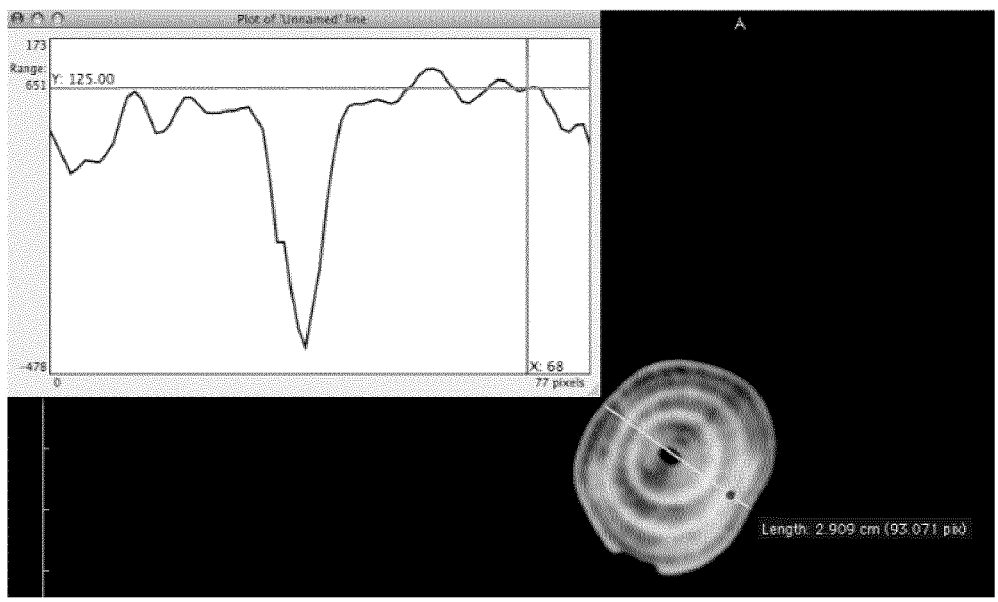
Figure 6:
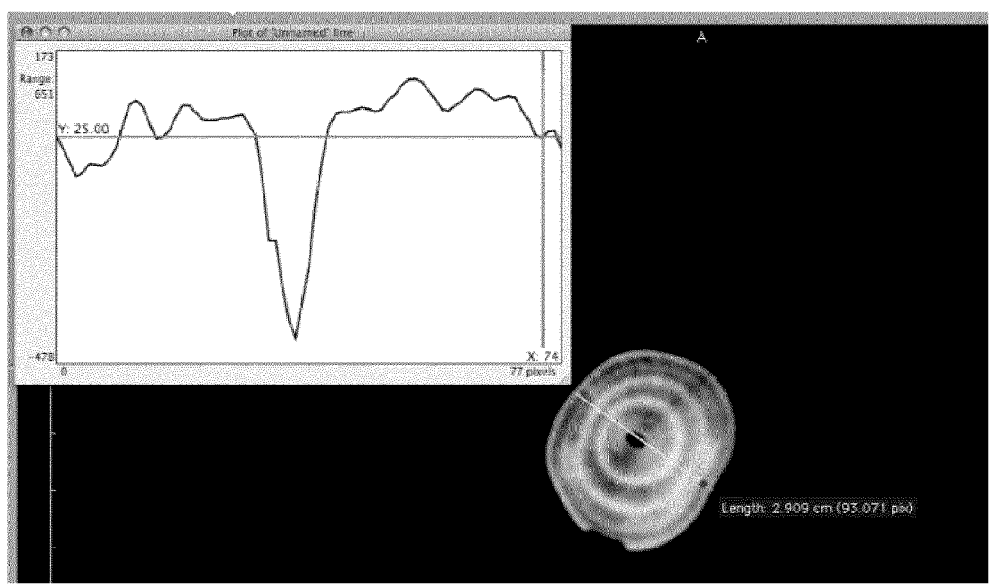

The very low radiodensity of the spot value of FIG. 6(c) corresponds to a region of soft, spongy pith material at the centre of the stem. The larger values (e.g. +119 and +125) correspond to typical radiodensity values observed in highly hydrated regions of healthy wood tissue.

Figure 7:
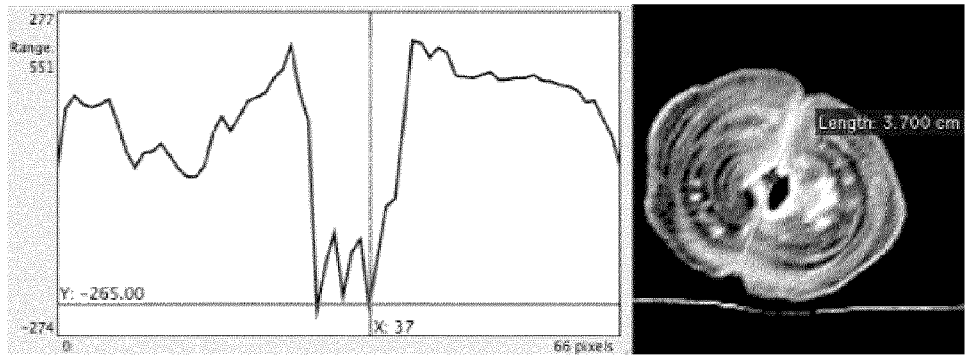
FIG. 7 is a series of tomographs and radiodensity graphs through esca-infected grapevine stems.
Figure 7:
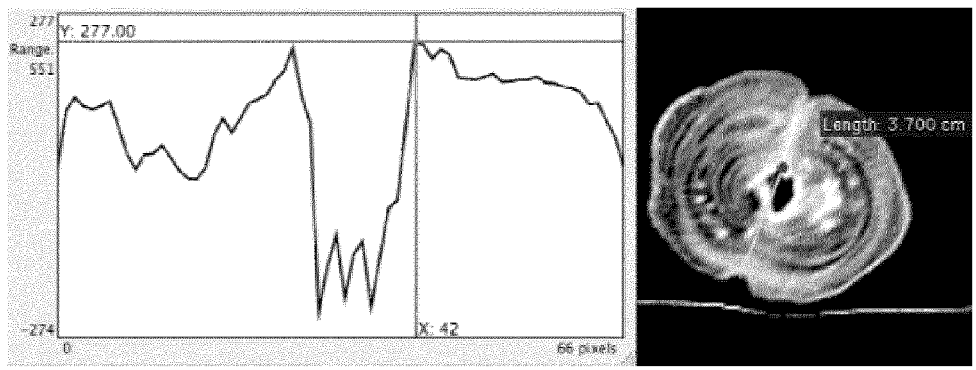
Figure 7:
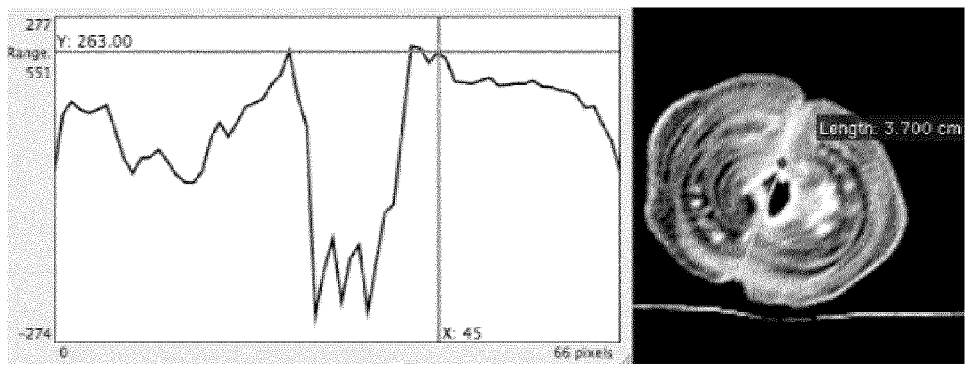
Figure 7:
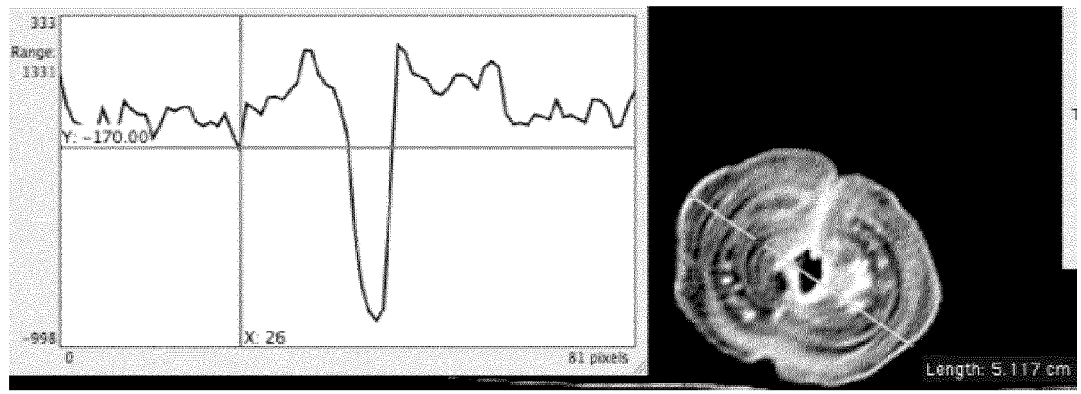
Figure 7:
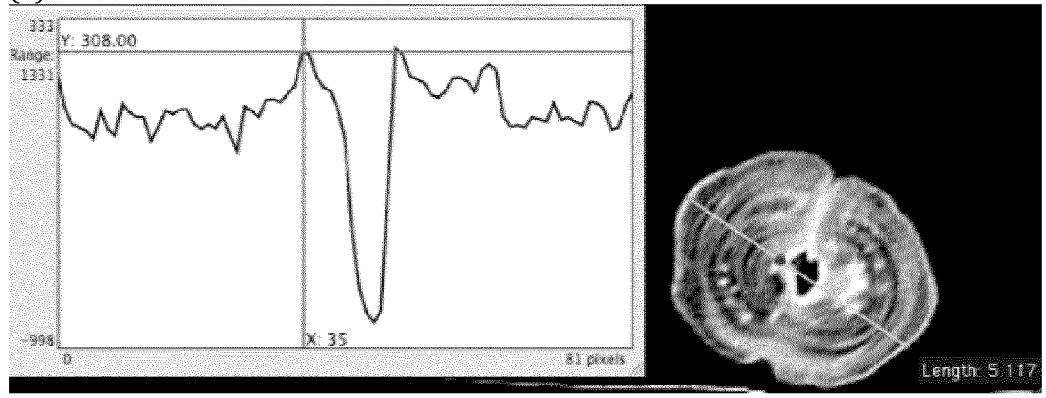
Figure 7:
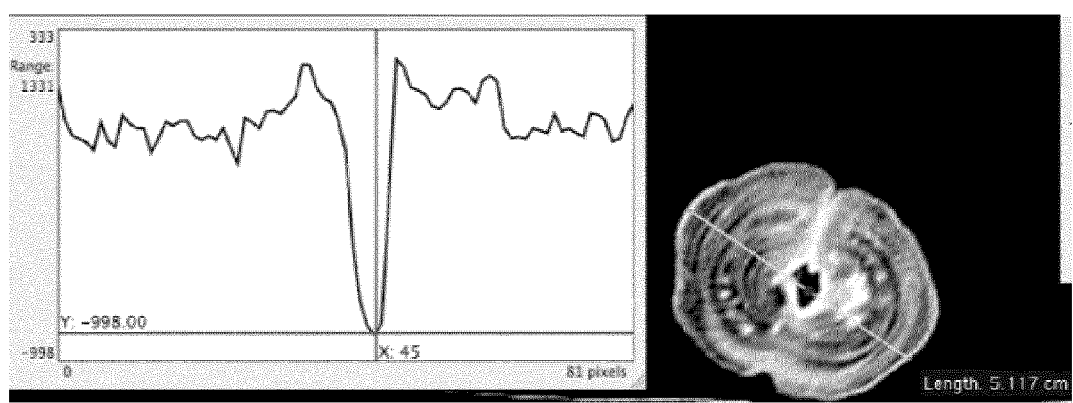
Figure 7:
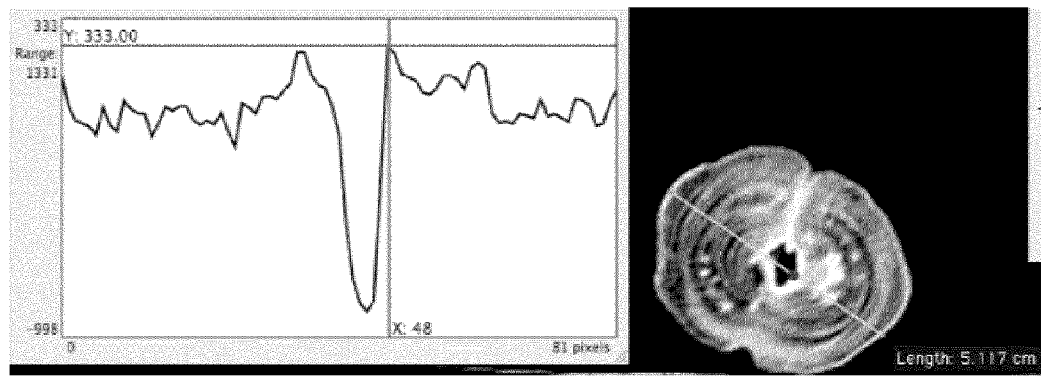
Figure 7:
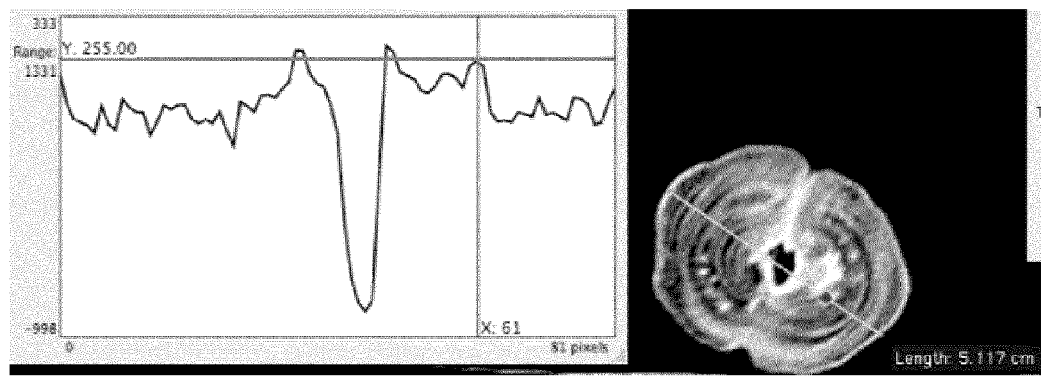
Figure 7:
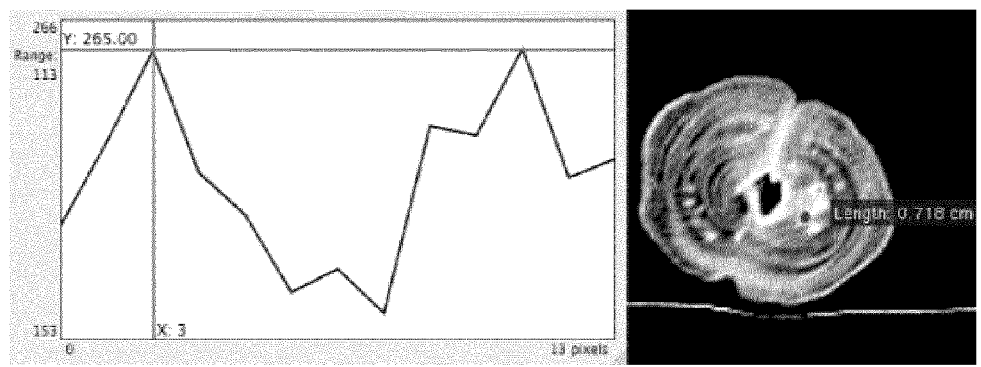
Figure 7:
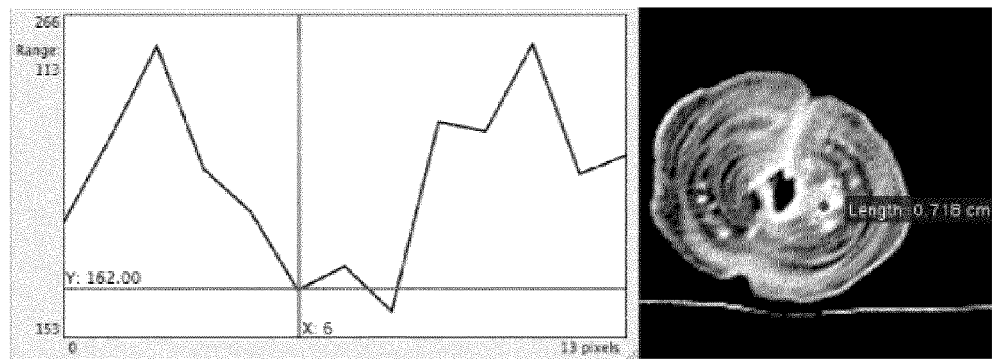
Figure 7:
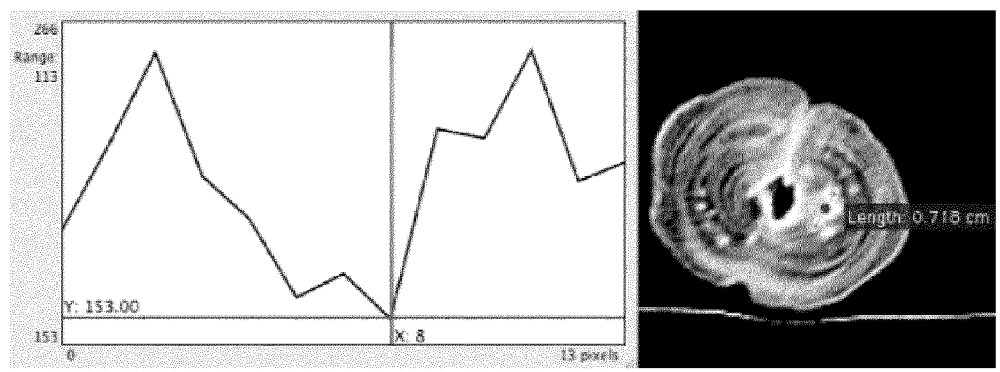
Figure 7:
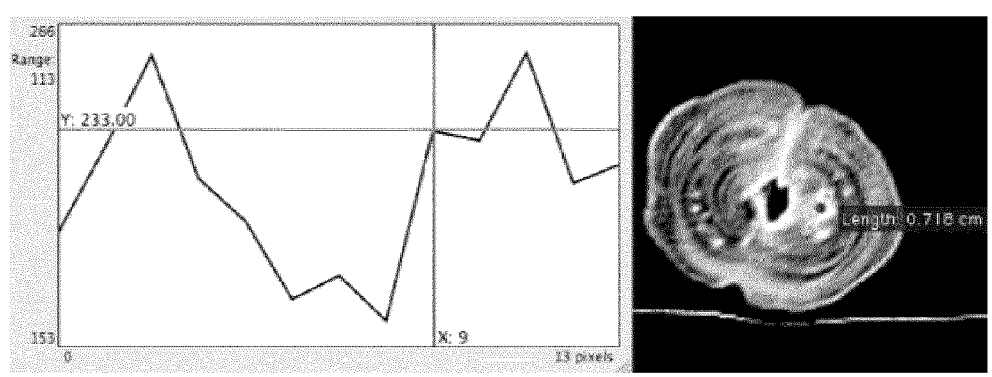

FIG. 7 (a)-(l) show patterns of radiodensity obtained by X-ray based computerised axial tomography in three sections of an esca-infected grapevine stem. The graphical representation of the radiodensity corresponds to the section illustrated on the 2-D tomographic image illustrated by a light-coloured line. Again, the spot on the 2-D image is represented by the vertical reference line on each graph, with the corresponding horizontal line giving the spot radiodensity measurement expressed in Hounsfield units.

In each graph, the range of radiodensities illustrated, and the "spot values" are as follows:

| FIG. | Y-axis minimum (Hounsfield) | Y-axis maximum (Hounsfield) | Spot Value (Hounsfield) |
|---|---|---|---|
| 7(a) | −274 | +277 | −265 |
| 7(b) | −274 | +277 | +277 |
| 7(c) | −274 | +277 | +263 |
| 7(d) | −998 | +333 | −170 |
| 7(e) | −998 | +333 | +308 |
| 7(f) | −998 | +333 | −998 |
| 7(g) | −998 | +333 | +333 |
| 7(h) | −998 | +333 | +255 |
| 7(i) | +153 | +266 | +265 |
| 7(j) | +153 | +266 | +162 |
| 7(k) | +153 | +266 | +153 |
| 7(l) | +153 | +266 | +233 |

The very high levels of radiodensity (typically above +250 Hounsfield in this particular example) correspond to regions where "black goo" has accumulated in the vasculature of the plant. The very low levels (typically the negative values in this example) correspond to regions corresponding to an "amadou", or to a hole or pith in the stem.

Analysis of the radiodensity from a large number of samples of grapevine wood in which features have been identified by subsequent sectioning have revealed the typical ranges of radiodensity observed in this species for various botanical features, or features of esca infection. These values are given in Table 1.

TABLE 1

Typical Radiodensity of Features in Grapevine

| Feature | Radiodensity (mean +/− S.D.) Hounsfield Units |
|---|---|
| Pith and Hole | −900 ± 50 |
| "Amadou" | −840 ± 70 |
| Dead affected wood | −450 ± 123 |
| Empty vessels | −109 ± 48 |
| Healthy wood | 80 ± 32 |
| Knots | 195 ± 77 |
| Black spots | 234 ± 56 |
| Brown Affected Wood | 294 ± 71 |

By use of X-ray tomographic imaging, followed by subsequent sectioning and identification of features, the skilled address may readily determine the typical range of densities for features in other woody species, and for other fungal infections. In this way, the techniques disclosed herein may be applied across a wide range of species and fungal infections.

FIGS. 8 to 12 show images obtained using high sensitivity computerised X-ray tomography of esca-infected grapevine (Vitis) stems at an early stage of infection, before external symptoms were apparent.

Figure 8:
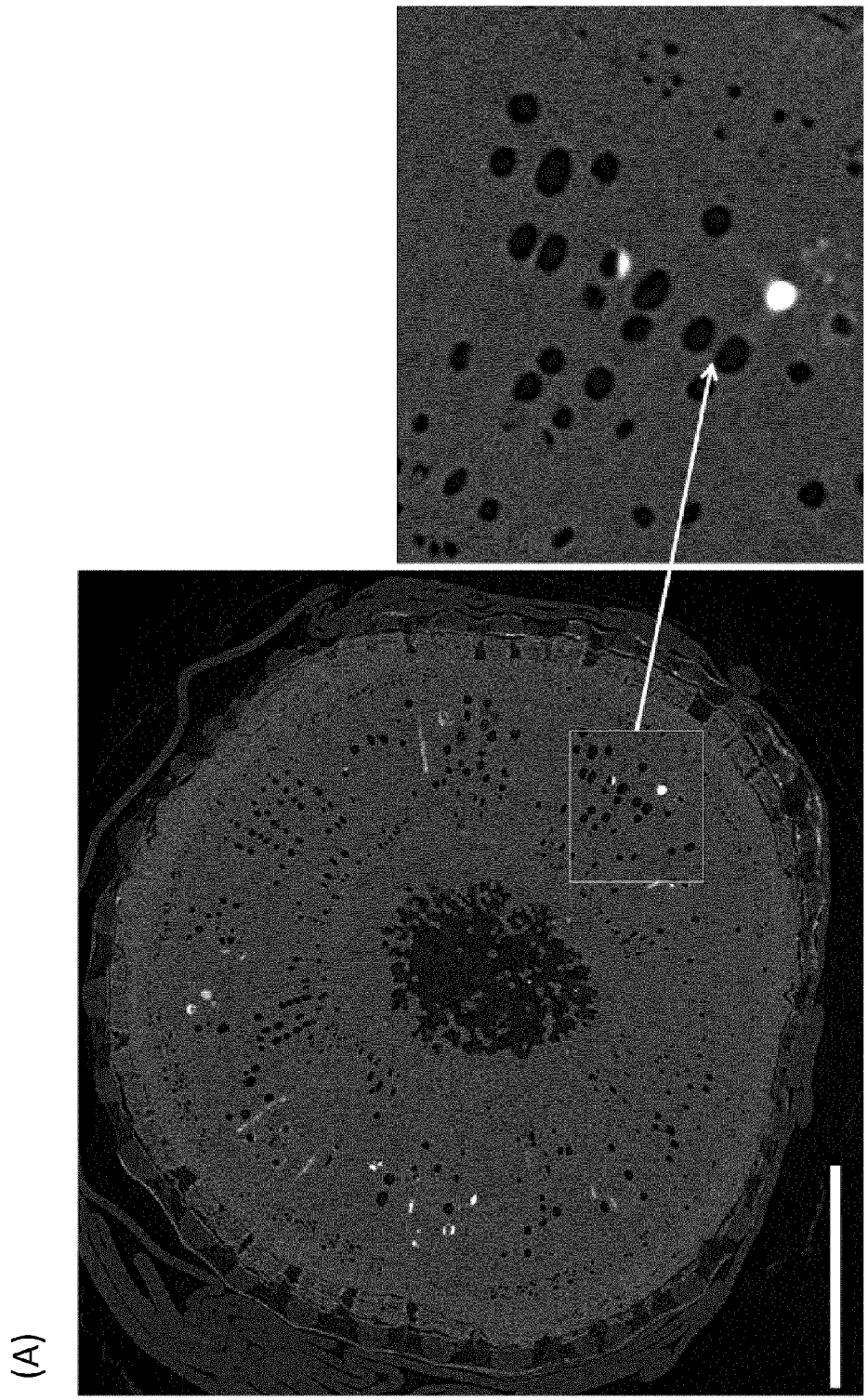
FIGS. 8 to 12 are X-ray microtomographic images through esca-infected grapevine stems.

FIG. 8 shows a cross-section (A) and detail (B) from a thin trunk of a two-year old grapevine infected with initial stages of esca. The scale bar represents 5 mm. The bright areas in the image represent regions of high radiodensity, indicative of the esca infection. The larger of the bright spots on the inset (B) has a diameter of approximately 250 microns, illustrating the surprising ability of the technique to visualise even early stages of esca infection.

Figure 9:
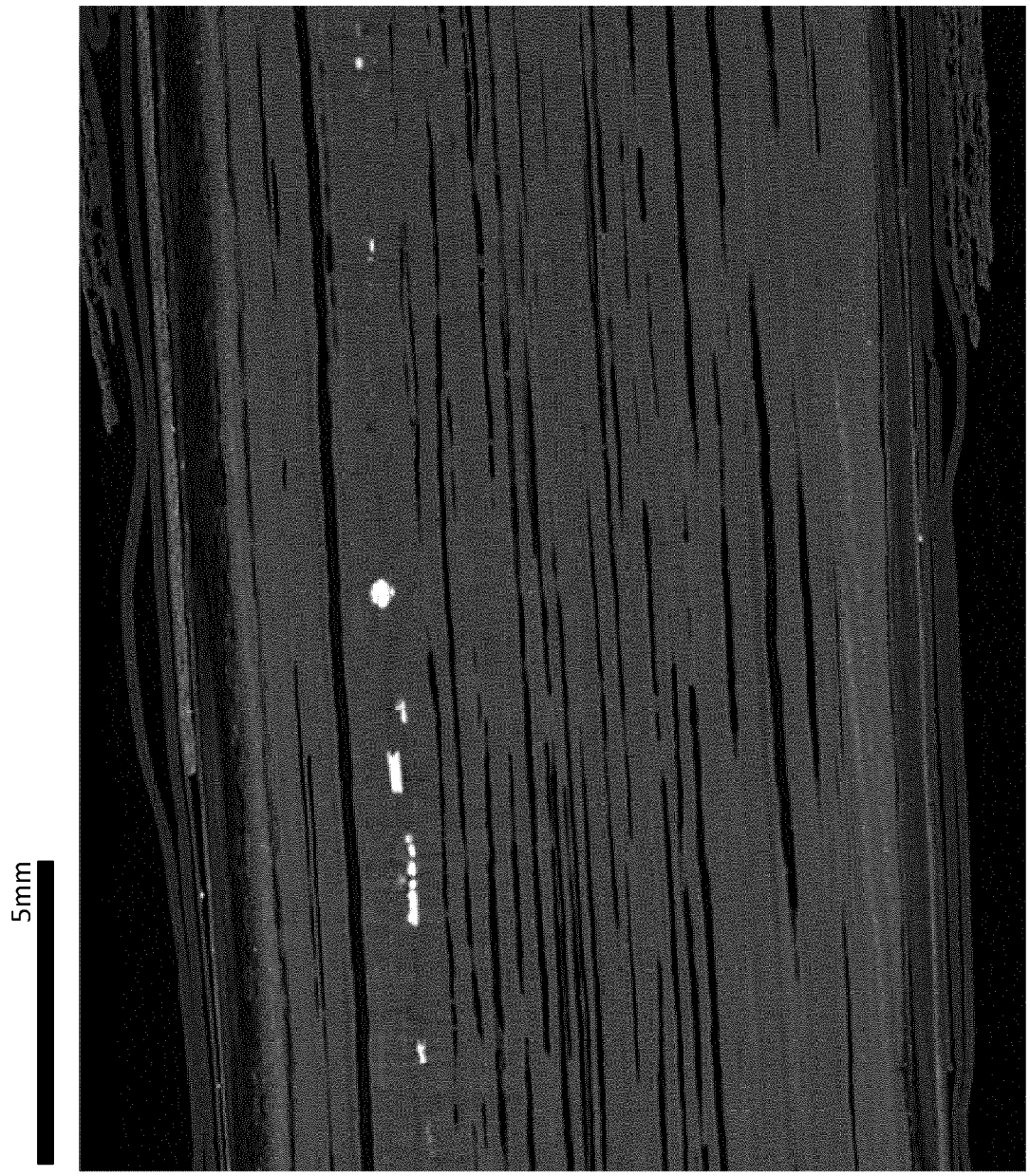

FIG. 9 shows a longitudinal cross-section X-ray tomographic image of a thin trunk from a two-year old grape vine (Vitis) infected with initial stages of esca. The scale bar represents 5 mm. The bright areas in the image again represent regions of high radiodensity, indicative of the esca infection. High radiodense regions as small as 50 microns can be seen in the images.

Figure 10:
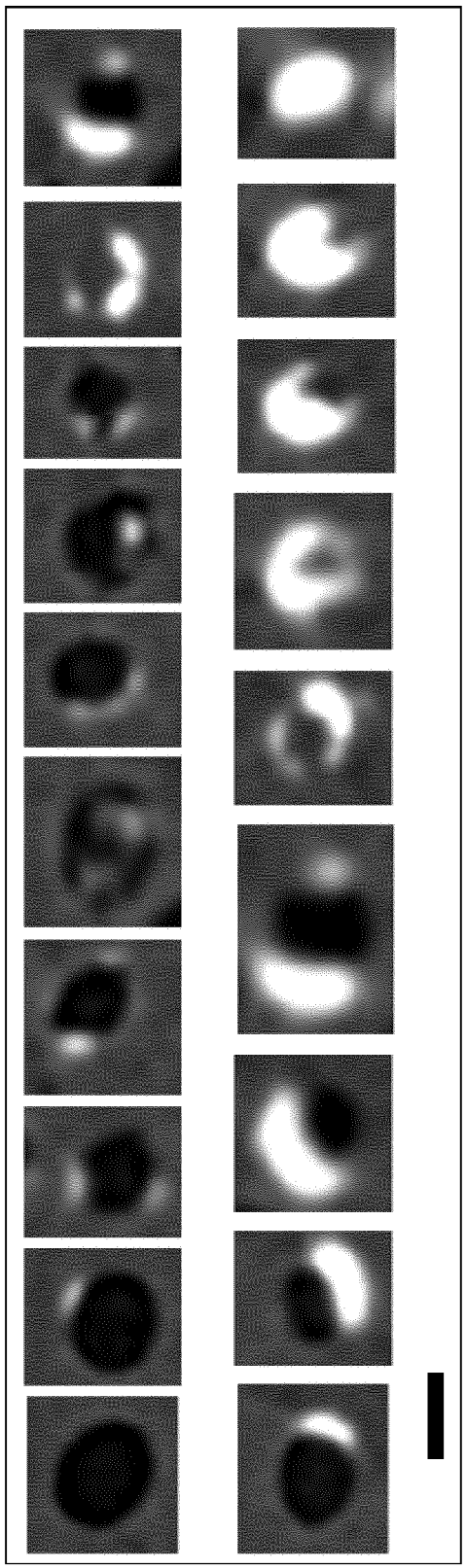

FIG. 10 shows X-ray tomographic images of xylem vessels with various degrees of filling by the "black goo" that characterises esca infection. The images are taken in a grapevine trunk during the initial, asymptomatic stages of esca infection. The scale bar represents 100 microns, again illustrating that very small infection-related features may be identified.

Figure 11:
Figure 12:

FIGS. 11 and 12 are 3-dimensional axial tomographic reconstructions of a grapevine (Vitis) trunk, highlighting its irregular shape. The scale bar represents 10 cm in FIG. 11 and 10.13 cm in FIG. 12.

The invention claimed is:

1. A method of detecting fungal infection in a woody plant comprising the steps of:

using X-ray tomographic imaging;

obtaining a tomographic image of a location of said woody plant comprising vasculature, said tomographic image comprising spatially-distributed measurements of radiodensity;

determining the presence or absence of regions within said image having a radiodensity higher than the radiodensity in the vasculature of a healthy plant;

the presence of such regions of high radiodensity being indicative of the presence of an early stage fungal infection in the vasculature of the plant when said plant is externally asymptomatic.

2. A method according to claim 1 wherein said woody plant is a plant of the genus *Vitis* or a hybrid thereof.

3. A method according to claim 1 wherein said woody plant is a plant of the genus *Actinidia* or a hybrid thereof.

4. A method according to claim 1 wherein said woody plant is a plant of the genus *Citrus* or a hybrid thereof.

5. A method according to claim 4 wherein said fungal infection comprises infection with *Phoma tracheiphila*.

6. A method according to claim 1 wherein said fungal infection causes accumulation of fluid in the xylem of said plant.

7. A method according to claim 1 wherein said fungal infection comprises one of Esca and an Esca-like disease.

8. A method according to claim 1 wherein said fungal infection comprises infection with *Eutypa lata*.

9. A method according to claim 1 wherein said fungal infection comprises *Botryosphaeria*-associated canker.

10. A method according to claim 1 wherein said tomography is one of axial X-ray tomography and X-ray microtomography.

11. A method according to claim 10 wherein said method determines the presence or absence of regions within said image having a radiodensity larger than a first predetermined radiodensity;

the presence of such regions of high radiodensity being indicative of the presence of said fungal infection.

12. A method according to claim 11 wherein said first predetermined radiodensity is the mean radiodensity of a corresponding region in an uninfected control plant.

13. A method according to claim 11 wherein said first predetermined radiodensity is 100, 120, 130, 140, 150, 160, 170, 180, 190 or 200 Hounsfield units.

14. A method according to claim 11 further comprising the step of:

determining the presence or absence of regions within said image having a radiodensity less than a second predetermined radiodensity;

the presence of both such regions of high and low radiodensity being indicative of the presence of an advanced stage of said fungal infection.

15. A method according to claim 14 wherein said second predetermined radiodensity is −200, −300, −400, −500, −600, −700, or −800 Hounsfield units.

16. A method according to claim 11 wherein said radiodense regions have a spatial dimension of less than 5 mm, 2 mm, 1 mm, 500 microns, 200 microns 100 microns or 50 microns.

17. A method according to claim 11 wherein said stem has a diameter of between 1 and 10 cm.

18. A method according to claim 11 wherein said woody plant comprises rootstock or graft material, and said stem has a diameter of less than 1 cm.

19. A method of control of fungal infection in woody plants comprising the steps of:

determining the presence or absence of said fungal infection using a method according to claim 1; and treating said woody plant with a fungicide if said fungal infection is so detected.

20. A method according claim 19 wherein said fungicide is injected into said plant.

21. A method according to claim 19 wherein said tomographic imaging is used to identify the location in the plant in which said fungal infection is present, and said fungicide is introduced at that location.

22. A method according to claim 19 wherein said fungicide is a systemic fungicide.

* * * * *